United States Patent [19]

Pawluskiewicz et al.

[11] Patent Number: 5,255,682
[45] Date of Patent: Oct. 26, 1993

[54] ULTRASONIC DIAGNOSTIC IMAGING SYSTEMS WITH SCANHEAD INDICATORS

[75] Inventors: Peter M. Pawluskiewicz; Perry W. Kaminski, both of Seattle, Wash.

[73] Assignee: Advanced Technology Laboratories, Inc., Bothell, Wash.

[21] Appl. No.: 613,334

[22] Filed: Nov. 14, 1990

[51] Int. Cl.⁵ .............................................. A61B 8/00
[52] U.S. Cl. .......................... 128/662.03; 128/661.01
[58] Field of Search ...................... 128/661.07–661.10, 128/660.01, 660.07, 662.03, 661.01, 662.06, 662.03

[56] References Cited

U.S. PATENT DOCUMENTS

| | | | |
|---|---|---|---|
| 4,543,959 | 10/1985 | Sepponen | 128/653.2 |
| 4,545,387 | 10/1985 | Balique | 128/660.01 X R |
| 4,587,972 | 5/1986 | Morantle, Jr. | 128/660.03 |
| 5,050,610 | 9/1991 | Oaks et al. | 128/662.06 |
| 5,088,497 | 2/1992 | Ikeda | 128/661.07 |
| 5,103,825 | 4/1992 | Hokanson et al. | 128/661.07 |

OTHER PUBLICATIONS

Hitachi Sales Brochure, excerpt from *Cardio*, Nov. 1990.
Rapoport, I. et al. "A Pilot Clinical PEP Monitor", *IEEE Trans. on Biomedical Engineering*, vol. BME-26 No. 6, Jun. 1979.

*Primary Examiner*—Francis Jaworski
*Attorney, Agent, or Firm*—W. Brinton Yorks, Jr.

[57] ABSTRACT

Ultrasonic diagnostic scanheads are described which include a lighting mechanism located at the transducer end of the scanhead. The scanhead includes an integral light which is illuminated when the scanhead is connected to an imaging system. The light is color-coded in a manner which clearly identifies a particular characteristic of the scanhead such as frequency of operation. In the preferred embodiment the integral light is located in a position on the scanhead which also informs the user of the orientation of the image plane in relation to the scanhead. In accordance with a further aspect of the present invention, the light of a selected scanhead is modulated by the imaging system when the clinician selects the scanhead for use.

19 Claims, 4 Drawing Sheets

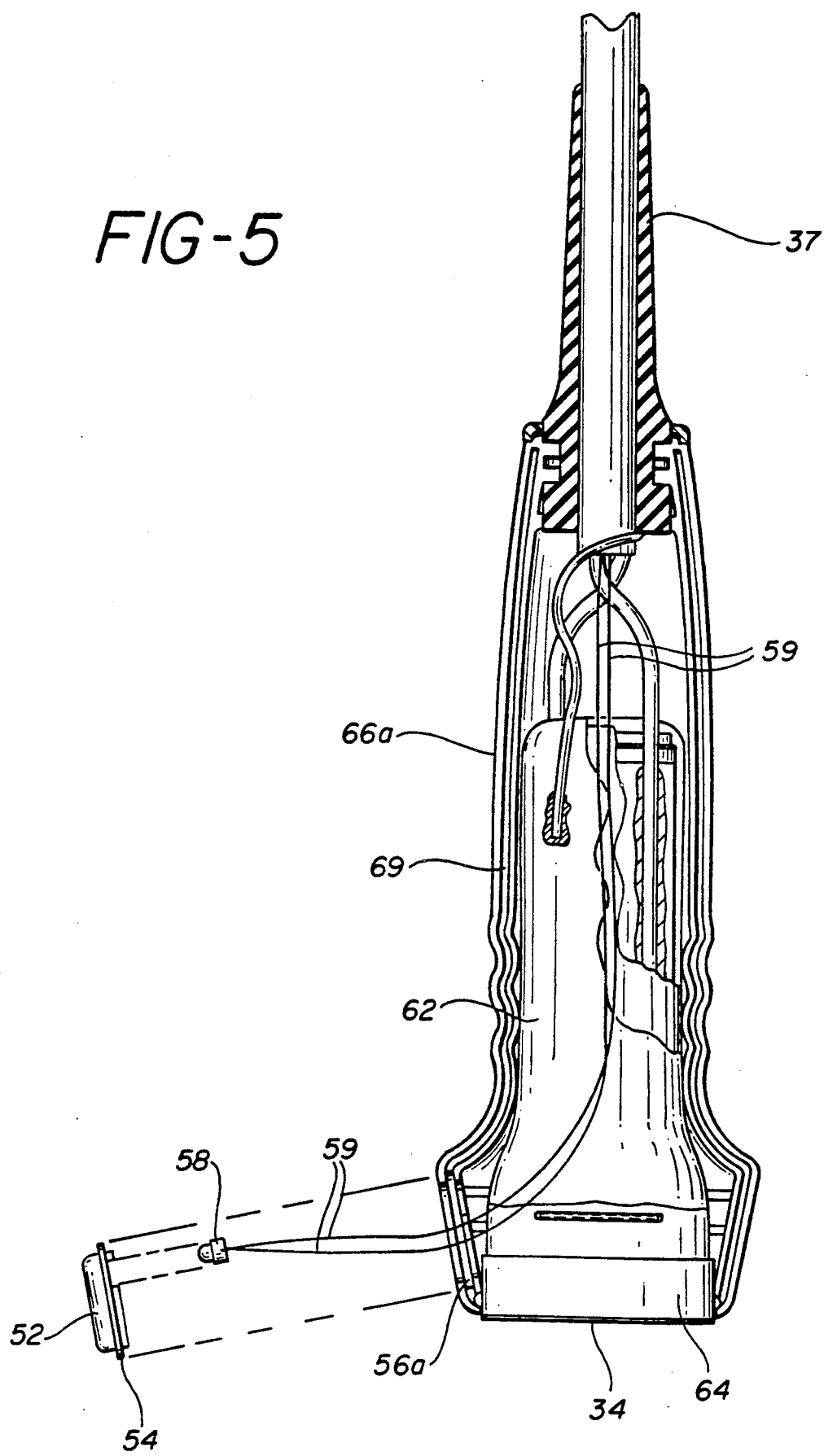

ULTRASONIC DIAGNOSTIC IMAGING SYSTEMS WITH SCANHEAD INDICATORS

This invention relates to ultrasonic diagnostic systems which utilize ultrasonic transducer scanheads to provide diagnostic information concerning a medical patient and, in particular, to the use with such scanheads of means for indicating scanhead characteristics to the user.

Ultrasonic diagnostic imaging systems are presently available which offer the clinician a wide variety of scanheads of differing clinical capability. For example, the Ultramark ® 9 diagnostic ultrasound system available from the assignee of the present application, Advanced Technology Laboratories, Inc. makes available to the clinician over twenty different types of scanheads, of which fourteen may be used for diagnostic imaging. Scanhead types may be classified according to the type of ultrasonic transducer employed in the scanhead for generation of transmitted ultrasonic waves and reception of echo information from tissue structure within the body, and by the image format in which the echo information is processed and displayed. These types include single and multielement array transducers, for instance, and array transducers may be configured as either linear or annular arrays. Various possible image formats include linear array, phased array, or sector formats.

Within each of these types of scanhead configurations and uses the scanheads may further be characterized by the frequency of operation of the ultrasonic transducer. The frequency of a transducer is conventionally described in terms of its center frequency. For example, phased array scanheads for the Ultramark 9 system are available with frequencies of 2.25, 3.0 and 5.0 Mhz. This wide variety of scanheads of differing performance characteristics provides the clinician with the ability to choose a scanhead which provides the best performance for a specific clinical application.

The ultrasonic imaging system conventionally displays real time images from the echo information received by the scanhead on a video monitor. In many instances the monitor is displaying a complex image of tissue structure in the body and the clinician is trying to discern fine details of pathology. In order to make the best possible diagnosis under these conditions, the clinician will frequently perform the ultrasound examination in a darkened or dimly lit room, thereby enhancing visual perception of the diagnostic detail of the image. As the clinician proceeds with the examination, he or she may find it necessary to change scanheads in order to use the specific scanhead with characteristics best matched to the anatomy being explored. The Ultramark 9 system facilitates examinations in such a situation, as the system enables a user to connect several scanheads to the imaging system simultaneously. When the decision is made to change scanheads, the clinician only has to touch the lighted keys on the system control panel necessary to select another pre-connected scanhead.

It has been found that even the provision of multiple scanhead connections on the imaging system can still leave dilemmas unsolved in the dimly lit examination room. In particular, it can be difficult to discern which among several connected scanheads is the scanhead which is to be used next. In a darkened room it can be difficult to locate the scanheads, then select the desired one. The problem can be even more acute when several scanheads of the same type but differing transducer frequencies are simultaneously connected to the system, for in that instance the physical characteristics of the scanheads, even when viewed in a lighted area, are virtually the same.

In accordance with the principles of the present invention, an ultrasonic imaging system scanhead includes means for identifying the scanhead in a dimly lit room. In a preferred embodiment, the scanhead includes an integral light which is illuminated when the scanhead is connected to the imaging system. The light is color-coded in a manner which clearly identifies a particular characteristic of the scanhead such as frequency of operation. In the preferred embodiment the integral light is located in a position on the scanhead which also informs the user of the orientation of the image plane in relation to the scanhead. In accordance with a further aspect of the present invention, the light is colored by a colored lens, thereby passively indicating the scanhead characteristic even when the scanhead is not connected to the imaging system. In accordance with yet another aspect of the present invention, the light of a selected scanhead is modulated by the imaging system as by increasing its intensity when the clinician selects the scanhead for use.

In the drawings:

FIG. 5 is a partial cross-sectional view of the scanhead of FIG. 3; and

Figure 1:
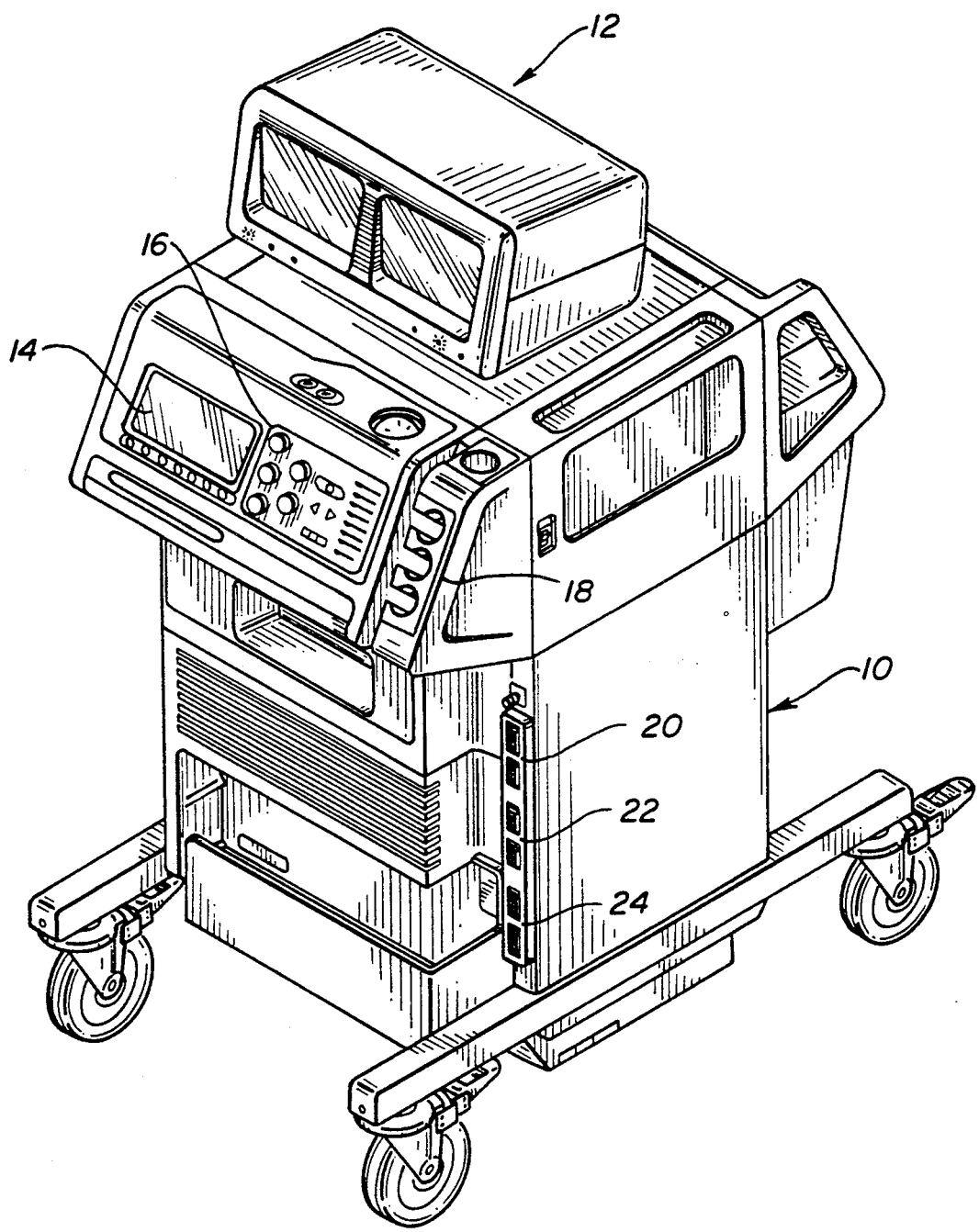
FIG. 1 is a perspective view of an ultrasonic imaging system suitable for use with scanheads of the present invention.

Referring first to FIG. 1, an ultrasonic diagnostic imaging system 10 suitable for use with scanheads of the present invention is shown in a perspective view. The main body of the system contains the computer controlled electronics which operate and control all aspects of system operation. Located on top of the body is a dual monitor module 12 which houses a color imaging monitor and a monochrome imaging monitor. On the front of the body of the system is a control panel, including an illuminated touch-sensitive plasma control panel 14. During operation of the system, "soft key" menus are displayed on the plasma control panel, which the user touches to actuate or select the function displayed at the location which the user touches. To the right of the plasma control panel are a number of manual user controls 16 for such performance characteristics as gain, image freeze, VCR control, and image depth settings. To the right of the manual controls is a scanhead holder 18, with cylindrical compartments for holding three scanheads.

Below the scanholder holder 18 are three connector jacks 20, 22, and 24 into which the connector of a scanhead may be plugged. Up to three scanheads may be plugged into the connector jacks simultaneously and any one of the three scanheads may be selected for use by pressing the scanhead select keys on the plasma display menu for scanhead selection. Image data from the selected scanhead is then processed by the system electronics and the resultant image is displayed on one or both of the monitors.

Figure 2A:
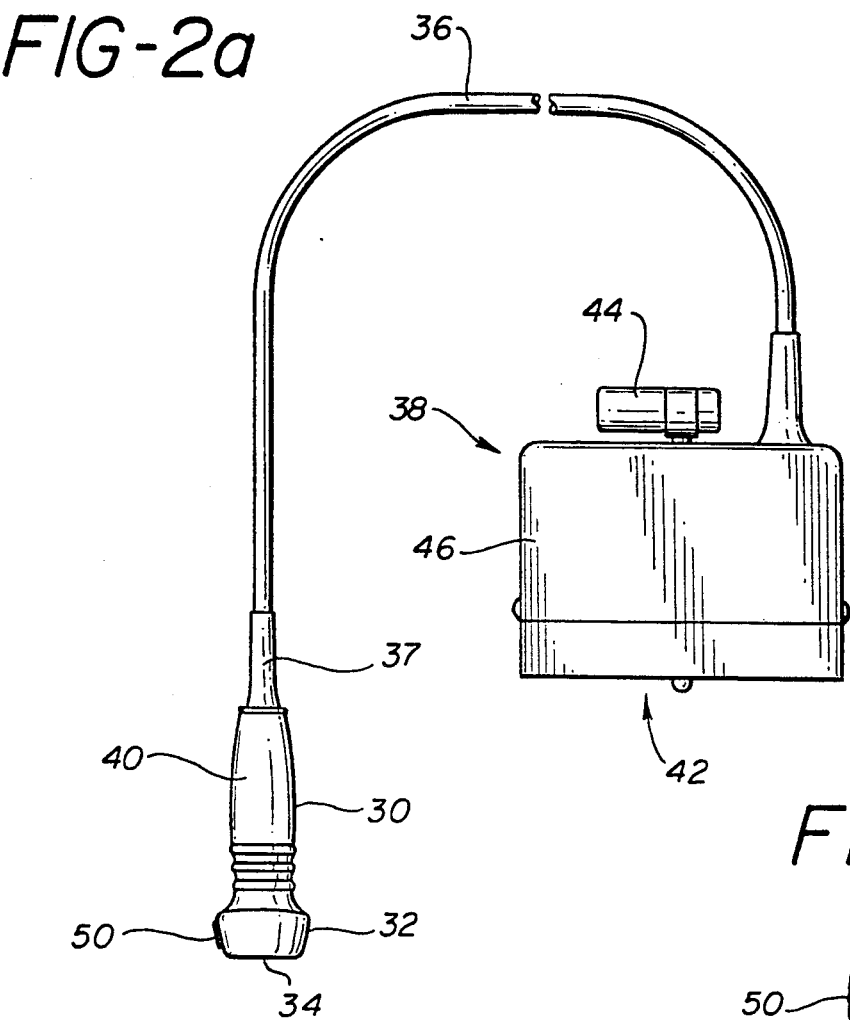
FIGS. 2a and 2b are side and plan views of a scanhead constructed in accordance with the principles of the present invention.
Figure 2B:
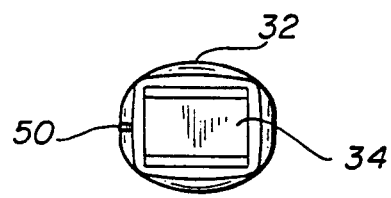

Referring to FIGS. 2a and 2b, a scanhead constructed in accordance with the principles of the present invention and suitable for use with the imaging system of FIG. 1 is shown. The scanhead there shown comprises a handle end 30, a connector end 38, and a wiring cable 36 connecting the handle end and the connector end. The handle end comprises a hollow case 40 which houses a piezoelectric transducer within its distal end 32. The transducer transmits ultrasonic energy and receives ultrasonic echoes through the face 34 of the scanhead. Also located within the case 40 are electronic tuning elements for the transducer and electrical connections between the transducer and the wires of the cable. A strain relief 37 is located at the point where the cable 36 enters the case 40. The transducer converts received ultrasonic echoes to electrical signals which are transmitted through the wires of the cable to an electrical connector at the connector end of the scanhead.

The electrical connector at the connector end of the scanhead, indicated by the arrow 42, is enclosed in a connector case 46. The wires of the cable are connected within the case 46 to pins of the connector. The connector case 46 also houses a programmable read-only memory (PROM) which is connected to some of the pins of the connector. The connector may be plugged into any one of the jacks 20-24 of the imaging system, whereby the pins of the connector engage mating sockets in the jack for the transfer of electrical signals between the transducer and PROM and the imaging system.

In accordance with the principles of the present invention, the handle end of the scanhead also includes a lighting mechanism 50. Preferably, the lighting mechanism is located at a position on the scanhead which indicates orientation of the scanhead with respect to the image on the monitor when the scanhead is in use. In this embodiment the transducer within the scanhead scans an area in front of the face of the transducer from left to right in the drawing. When an image of the scanned area is produced on the monitor, a visual marker is producer to the left of the planar image. The clinician, by seeing or tactilely feeling the location of the lighting mechanism on the scanhead, will then know how to position the scanhead during scanning so that the image is correctly oriented in relation to the patient.

Figure 3:
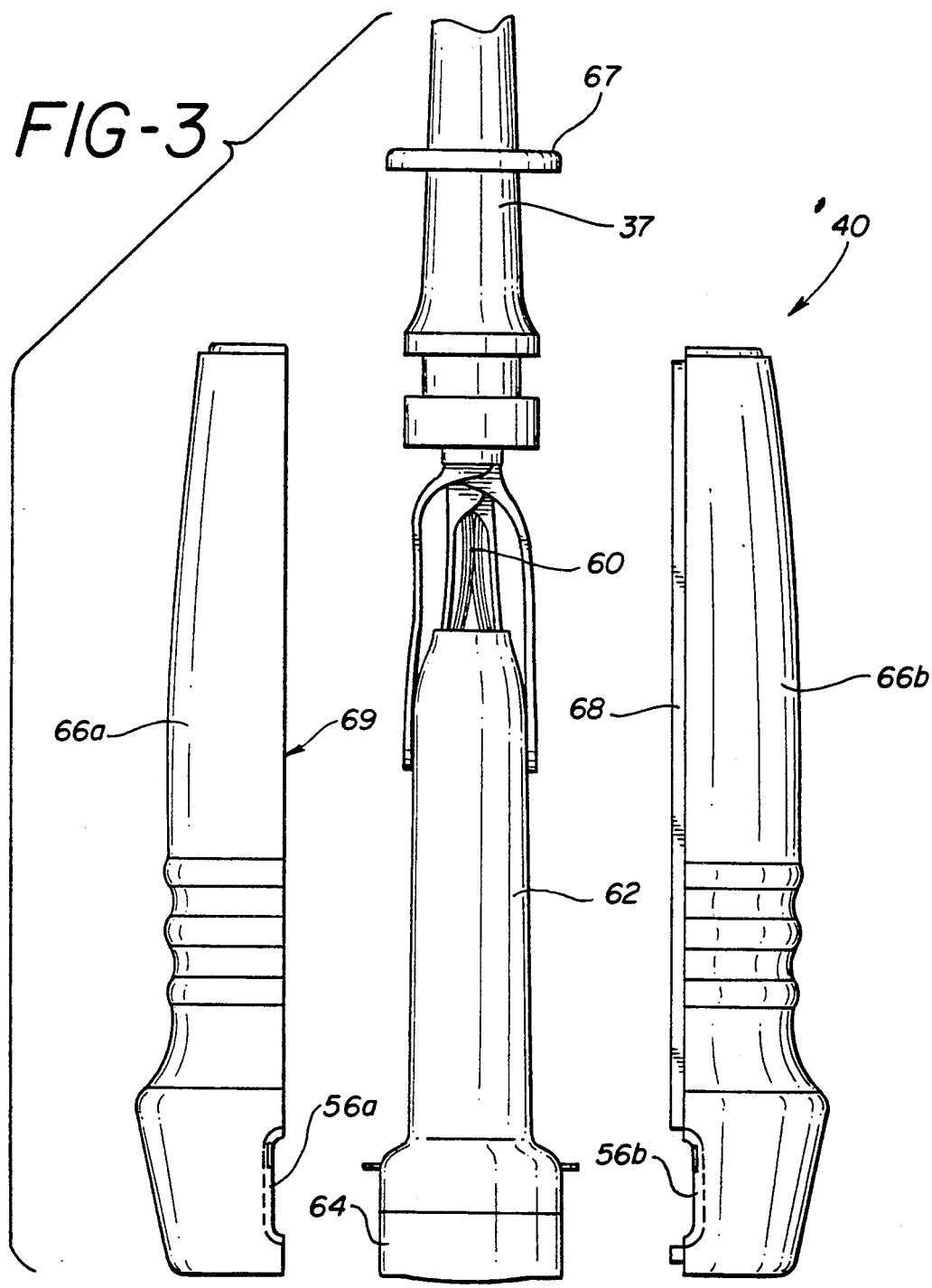
FIG. 3 is an assembly drawing of the transducer portion of the scanhead of FIGS. 2a and 2b.

FIG. 3 is a assembly drawing of the handle end of the scanhead of FIGS. 2a and 2b. The case 40 comprises two mating halves 66a and 66b. When the two halves are joined together the flange on case half 66b fits inside a corresponding groove 69 of case half 66a. The case thereby encloses the trnsducer 64 which is mounted at one end of a housing 62 which contains tuning elements for the transducer and the connections of wires 60 of the cable to the tuning elements and the transducer. When the case is closed the proximal end of the case engages the cable strain relief 37, and a color-coded retaining ring 67 fits over flanges at the rear of the case halves to secure the rear of the case about the strain relief. The retaining ring 67 is color-coded with the same color as the lighting mechanism 50, as discussed below.

Figure 4A:
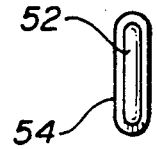
FIGS. 4a and 4b illustrate the light assembly for the scanhead of FIG. 3.
Figure 4B:
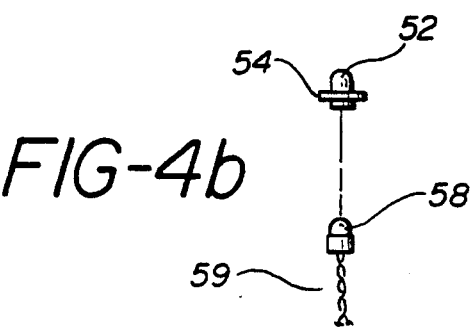

The case also defines a grooved opening for the lighting mechanism 50. The two halves of the opening are indicated at 56a and 56b, which define a generally oval opening when the case halves are joined together. The lighting mechanism contained within this opening is illustrated in FIGS. 4a and 4b, and includes a colored translucent lens 52 surrounded by a flange 54. A bulb or light emitting diode (LED) 58 fits within the lens as shown in FIG. 4b. The flange 54 then engages the groove of the opening 56a,56b such that the lens 52 is projecting slightly from the side surface of the closed case to provide the tactile sensation described above. The mounting of the lighting mechanism in the case is further illustrated in FIG. 5, which shows the positioning of the mechanism in case half 66a and routing of the wires 59 of the LED into the cable. The LED wires 59 continue through the cable 36 and are connected to pins of the connector 42.

As mentioned above, the lens 52 is colored. It is alternatively possible to produce light of a desired color through the use of a colored LED and a colorless lens. LED's are commercially available in red, orange, and green for this purpose, for instance. In a preferred embodiment of the present invention, however, the lens is colored, thereby enabling the user to visually note the color of the lighting mechanism even when the scanhead is not energized by connection to the imaging system. In accordance with the principles of the present invention, the color of the lighting mechanism indicates a scanhead characteristic to the user.

In a preferred embodiment the scanhead characteristic indicated by the lighting mechanism is the frequency of the transducer. The colors chosen for this encoding are the well-known resistor color code of black=0, brown=1, red=2, orange=3, yellow=4, green=5, blue=6, violet=7, gray=8 and white=9. The color used for a particular scanhead represents one of the resistor coding numbers which matches the first digit of the transducer frequency. For instance, a scanhead with a 2.25 MHz transducer would emit red light. A scanhead with a 5.0 MHz transducer emits green light, a scanhead with a 3.5 MHz transducer emits orange light, and a scanhead with a 7.0 MHz transducer emits violet light. Thus, the color of the lens or the emitted light immediately indicates the frequency of the scanhead to the user by employing a well known color coding scheme.

Figure 6:
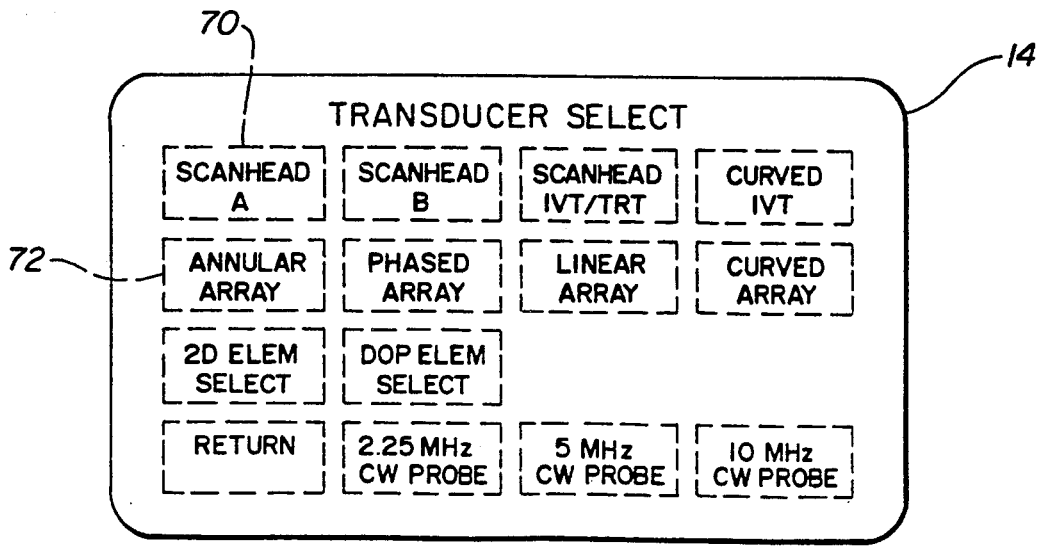
FIG. 6 is an illustration of the touch-sensitive plasma display panel of the imaging system of FIG. 1.

Referring to FIG. 6, a generic scanhead selection menu that is displayed on the plasma display panel 14 of the imaging system is shown. All of the annotation of this drawing, including the dashed boxes 70, 72 which define the soft keys of the panel, and the characters contained within the key locations, appear in illuminated form on the display panel. To select an annular array transducer, for example, the user touches the panel inside the soft key box 72 and the system then electronically connects the annular array scanhead to the processing and control electronics of the imaging system so that images from the annular array scanhead are processed for display on the system monitors.

From the foregoing, the advantages gained through use of the scanheads of the present invention in a diagnostic imaging procedure may be appreciated. Assume that the clinician wants to perform a radiology examination using phased array scanheads which physically appear as shown in FIG. 2. Further assume that the clinician is not initially certain of the optimal transducer frequency for the procedure, and hence desires to have three scanheads available: a 2.25 MHz scanhead, a 5.0 MHz scanhead, and a 7.0 MHz scanhead. These three scanheads are identified by noting the color of the lenses of the lighting mechanism, red, green, and violet, or by the color of the retaining ring at the rear of the case. The connectors of the scanheads are plugged into the jacks of the imaging system, and the handle ends of the scanheads are placed in the scanhead holder 18 with the scanning faces 34 directed upward.

The clinician prepares the patient for the procedure, calls up the scanhead selection menu on the plasma display panel, and dims the room lights to better view the monitors. With the scanheads plugged into the imaging system, the LED's are energized and the three colored lights of the scanheads may be easily distinguished in the darkened room. Prior to or at the time that the scanhead selection menu is displayed on the plasma panel, the imaging system polls the PROM of each connected scanhead and reads digital data into the imaging system which identifies the types of scanheads. This information is displayed by system within the dashed boxes of the soft keys. In this example, three of the soft keys will display "2.25 MHZ Phased Array", "5.0 MHz Phased Array", and "7.0 MHz Phased Array". The clinician now touches the soft key of the scanhead which is to be used first.

Once the clinician touches the panel to select a scanhead, the imaging system proceeds to electrically connect the scanhead to the imaging system electronics, and to electronically configure the control, processing, and software components of the system for operation specifically tailored to the desired scanhead. This initialization procedure is aided by test and calibration data contained in the PROM of the selected scanhead, and this data is read by the system and used in the initialization process. During initialization the scanhead is not ready for use, and, in accordance with the present invention, the light of the selected scanhead is modulated by the imaging system while initialization is underway. For instance, the light of the selected scanhead is flashed or blinked on and off at this time. Guided by the flashing light, the clinician can easily locate the selected scanhead in the darkened room and remove it from the scanhead holder to begin using it. When initialization is complete, the imaging system stops the blinking of the light, which is once again continuously illuminated. When the flashing stops, the clinician is informed that he or she may proceed with the diagnostic procedure. The light now is used during the procedure to indicate the orientation of the scanhead in relation to the displayed image, and provides both a visual and a tactile indiction of orientation.

In a cardiology application the modulation of the lighting mechanism may be done differently, as cardiology procedures generally involve fewer scanheads than radiology applications. A cardiologist may have only two scanheads connected to the imaging system at the outset of the procedure, for instance. In this application the lighting mechanisms of the scanheads would not be continuously illuminated as above, but would only be illuminated when a scanhead is selected. Upon selection the lighting mechanism of the selected scanhead would be illuminated continuously, or alternatively the lighting mechanism would blink during the initialization procedure, then remain continuously illuminated once the scanhead and system are ready for use.

What is claimed is:

1. A scanhead for an ultrasonic diagnostic imaging system which facilitates location of the scanhead in a darkened examination room, said scanhead comprising:
   a connector end including a connector for electrical connection of said scanhead to said diagnostic imaging system;
   a handle end including a piezoelectric transducer at a face which contacts a patient's body for receiving ultrasonic energy through said patient contact face and converting said energy to electrical signals which are used by said ultrasonic diagnostic imaging system to form an image of the internal structure of a portion of the patient's body which is located in front of said patient contact face;
   a cable connecting said connector end and said handle end to enable transmission of electrical signals between said transducer and said diagnostic imaging system; and
   an illumination mechanism located at said handle end of said scanhead in a predetermined position with respect to the spatial location of the plane of said image for emitting light from said scanhead, which light indicates a characteristic of said scanhead to a user during use of said scanhead.

2. The scanhead of claim 1, wherein said illumination mechanism is color coded to indicate an operating characteristic of said scanhead.

3. The scanhead of claim 2, wherein said illumination mechanism includes a lighting device which emits light of a predetermined color.

4. The scanhead in claim 1, wherein said illumination mechanism emits light of a predetermined color, said color indicating an operating characteristic of said scanhead.

5. The scanhead of claim 1, wherein said transducer is operated to scan an area in front of said handle end in a predetermined direction, and wherein said illumination mechanism is located at a position on said handle end which is indicative of said predetermined scanning direction of said transducer.

6. The scanhead of claim 5, wherein said illumination mechanism presents a physical discontinuity with respect to the surrounding material of said handle end so that the location of said illumination mechanism may be tactilely sensed.

7. The scanhead of claim 1, wherein said illumination mechanism is located on a surface of said handle end of said scanhead other than said face, said illumination mechanism being visible to a user of said scanhead during use of said scanhead.

8. The scanhead of claim 7, wherein said illumination mechanism is oriented in a direction away from the body being imaged during use of said scanhead.

9. The scanhead of claim 1, wherein said scanhead characteristic indicated by said light is a transmit frequency of said piezoelectric transducer.

10. The scanhead of claim 1, wherein said scanhead characteristic indicated by said light is the selection of said scanhead for image display by said diagnostic imaging system.

11. The scanhead of claim 1, wherein said scanhead characteristic indicated by said light is the orientation of said scanhead in relation to the image displayed by said diagnostic imaging system.

12. A scanhead for an ultrasonic diagnostic imaging system which facilitates location of the scanhead in a darkened examination room, said scanhead comprising:
   a connector end including a connector for electrical connection of said scanhead to said diagnostic imaging system;
   a handle end including a piezoelectric transducer for receiving ultrasonic energy and converting said energy to electrical signals;

a cable connecting said connector end and said handle end to enable transmission of electrical signals between said transducer and said diagnostic imaging system; and an illumination mechanism located at said handle end of said scanhead for emitting light from said scanhead, wherein said illumination mechanism includes an outer colored lens which provides color coding; to indicate an operating characteristic of said scanhead, and wherein said illumination mechanism includes an outer colored lens which provides said color coding.

13. An ultrasonic diagnostic system, comprising:

a scanhead including a transducer end, a connector end, and cable means connecting said transducer end and said connector end, said transducer end including an ultrasonic imaging transducer which opposes a face surface through which ultrasonic energy is transmitted and received, and an illumination mechanism located at said transducer end on a surface of said transducer end other than said face surface and which is visible to a user during use of said scanhead; and an operating and control system for energizing and controlling the operation of said scanhead and for forming an image of the interior of a body in response to the ultrasonic energy received by said imaging transducer, said operating and control system including means for connecting with said connector end of said scanhead and means for energizing said illumination mechanism during use of said scanhead to indicate an operating characteristic of said scanhead to a user.

14. The ultrasonic diagnostic system of claim 13, wherein said means for energizing said illumination mechanism includes means for modulating the energization of said illumination mechanism during a predetermined operating condition of said scanhead.

15. The ultrasonic diagnostic system of claim 14, wherein said predetermined operating condition is the selection of said scanhead for scanning.

16. The ultrasonic diagnostic system of claim 14, wherein said predetermined operating condition is the initialization of said operating and control system for energizing and controlling the operation of said scanhead.

17. The ultrasonic diagnostic system of claim 13, further comprising a second scanhead including a transducer end, a connector end, and cable means connecting said transducer end and said connector end, and an illumination mechanism located at said transducer end; wherein said operating and control system further including means for connecting with said connector end of said second scanhead and means for energizing said illumination mechanism of said second scanhead; and wherein said illumination mechanisms of said first named and second scanheads are color-coded for identification of an operating characteristic of said scanheads.

18. An ultrasonic diagnostic system, comprising:

a scanhead including a transducer end, a connector end, and cable means connecting said transducer end and said connector end, and an illumination mechanism located at said transducer end;

an operating and control system for energizing and controlling the operation of said scanhead, said operating and control system including means for connecting with said connector end of said scanhead and means for energizing said illumination mechanism;

further comprising a second scanhead including a transducer end, a connector end, and cable means connecting said transducer end and said connector end, and an illumination mechanism located at said transducer end; wherein said operating and control system further including means for connecting with said connector end of said second scanhead and means for energizing said illumination mechanism of said second scanhead; and wherein said illumination mechanisms of said first named and second scanheads are color-coded for identification of an operating characteristic of said scanheads, and wherein said operating and control system further includes means for selecting one of said first named and second scanheads for operation; and means for modulating the illumination mechanism of a selected scanhead.

19. An ultrasonic diagnostic system, comprising:

a scanhead including a transducer end, a connector end, and cable means connecting said transducer end and said connector end, and an illumination mechanism located at said an operating and control system for energizing and controlling the operation of said scanhead, said operating and control system including means for connecting with said connector end of said scanhead and means for energizing said illumination mechanism;

further comprising a second scanhead including a transducer end, a connector end, and cable means connecting said transducer end and said connector end, and an illumination mechanism located at said transducer end; wherein said operating and control system further including means for connecting with said connector end of said second scanhead and means for energizing said illumination mechanism of said second scanhead; and wherein said illumination mechanisms of said first named and second scanheads are color-coded for identification of an operating characteristic of said scanheads, and wherein said operating characteristic identified by said color-coding is transducer frequency; and wherein said color-coding numerically corresponds with the conventional color-coding of electrical resistors.

* * * * *